United States Patent [19]

Kummer et al.

[11] Patent Number: 5,352,228
[45] Date of Patent: Oct. 4, 1994

[54] APPARATUS AND METHOD TO PROVIDE COMPRESSION FOR A LOCKED INTRAMEDULLARY NAIL

[76] Inventors: Frederick J. Kummer; Kenneth Koval, both of 301 E. 17th St., New York, N.Y. 10017

[21] Appl. No.: 58,206

[22] Filed: May 10, 1993

[51] Int. Cl.⁵ ............................................. A61B 17/58
[52] U.S. Cl. ........................................ 606/64; 606/98
[58] Field of Search .................... 606/96, 80, 82, 60, 606/62, 64–67, 72, 98, 104

[56] References Cited

U.S. PATENT DOCUMENTS

| | | |
|---|---|---|
| 3,334,624 | 8/1967 | Schneider et al. |
| 3,439,671 | 4/1969 | Kuntscher |
| 3,717,146 | 2/1973 | Halloran |
| 4,103,683 | 8/1978 | Neufeld .................. 606/96 |
| 4,262,665 | 4/1981 | Roalstad et al. |
| 4,574,795 | 3/1986 | Georges |
| 4,590,930 | 5/1986 | Kurth et al. |
| 4,622,959 | 11/1986 | Marcus .................. 606/64 |
| 4,705,027 | 11/1987 | Klaue |
| 4,733,654 | 3/1988 | Marino |
| 4,781,181 | 11/1988 | Tanguy |
| 4,800,873 | 1/1989 | Audell .................. 606/62 |
| 4,911,153 | 3/1990 | Border .................. 606/64 |
| 4,913,137 | 4/1990 | Azer et al. .............. 606/64 |
| 4,919,679 | 4/1990 | Averill et al. ........... 606/62 |
| 5,032,125 | 7/1991 | Durham et al. .......... 606/62 |
| 5,057,110 | 10/1991 | Kranz et al. ............ 606/62 |

FOREIGN PATENT DOCUMENTS 1680129  9/1991  U.S.S.R. .................. 606/62

Primary Examiner—Tamara L. Graysay
Attorney, Agent, or Firm—Stephen E. Feldman

[57] ABSTRACT

An apparatus for the fixation of a bone and a method for locking an intramedullary nail. The bone has a medullary canal for use with an intramedullary nail that has been inserted into the medullary canal, the intramedullary nail having a longitudinal axis and distal and proximal ends and apertures in the ends. It essentially comprises a first member in the form of a sliding tubular member, a compression assembly, a guide member and an alignment fixture. The first member is in the form of an elongated first element having first and second ends, a central aperture, and a longitudinal axis aligned with the longitudinal axis of the intramedullary nail. The first end engages the bone adjacent the proximate end of the intramedullary nail. The compression assembly bears against the second end of the first element and applies compressive force to the bone through the first element. The guide member is disposed parallel to and spaced apart from the intramedullary nail; it has a proximal end and a proximal aperture. The alignment fixture is connected to the guide member and the first element and aligns the guide member with respect to the intramedullary nail to position the axis of the proximal aperture in the guide member along axis of the proximal aperture in the intramedullary nail.

16 Claims, 3 Drawing Sheets

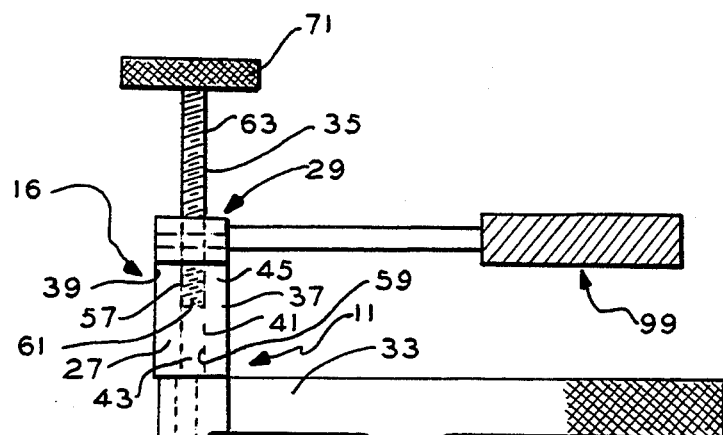
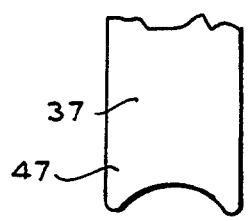
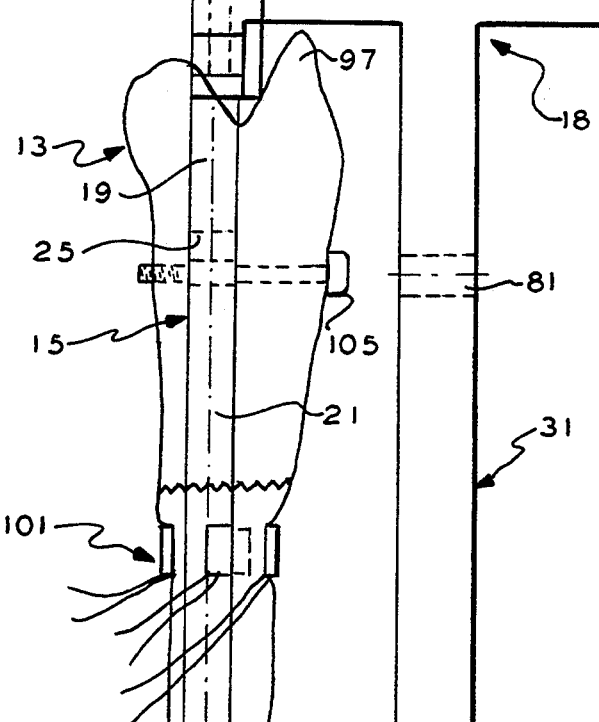
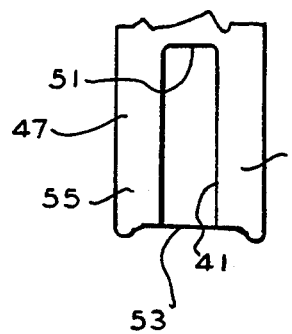
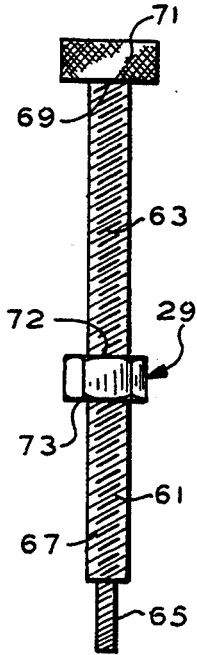

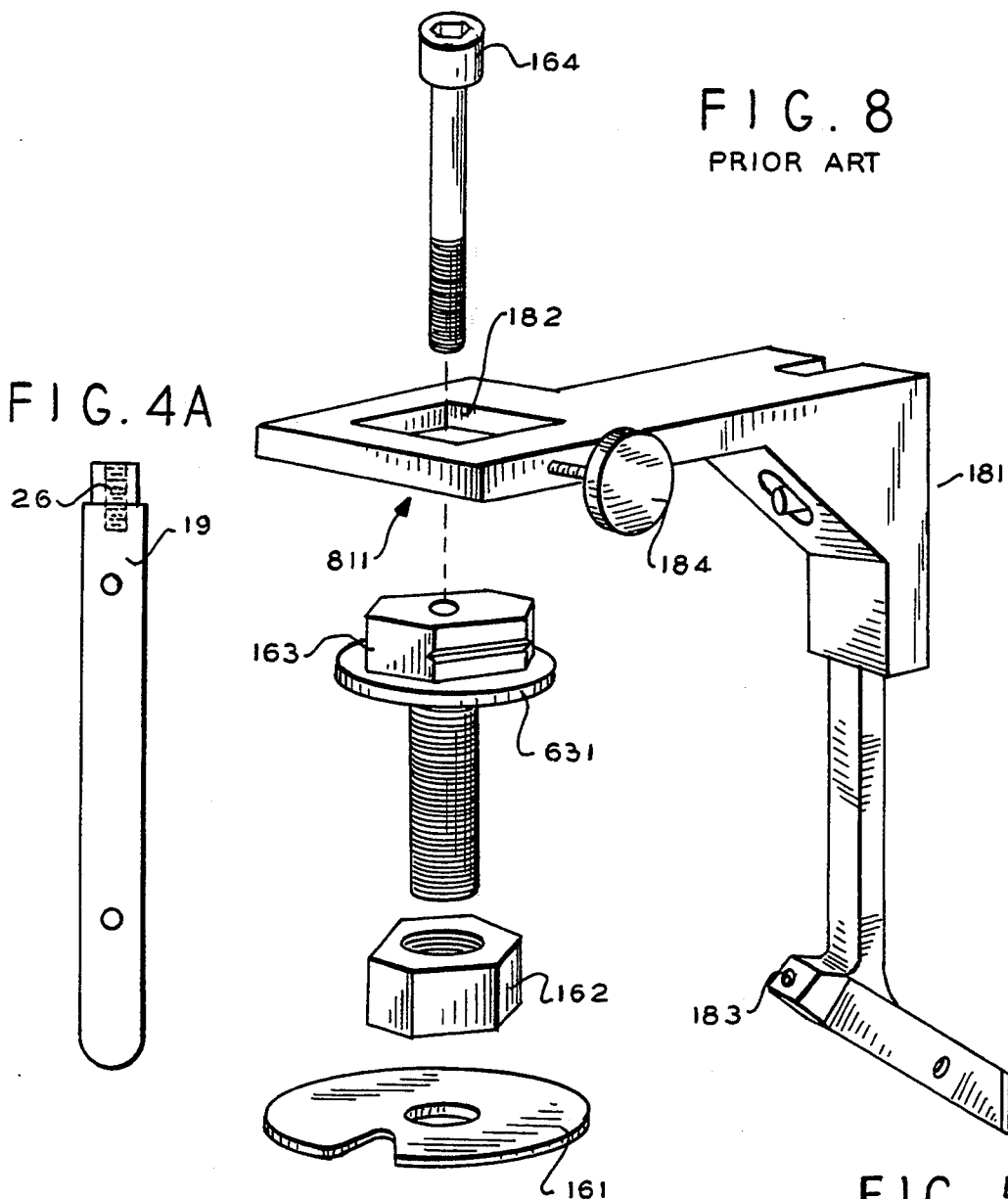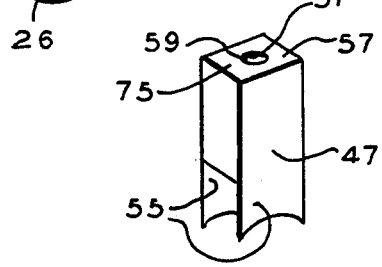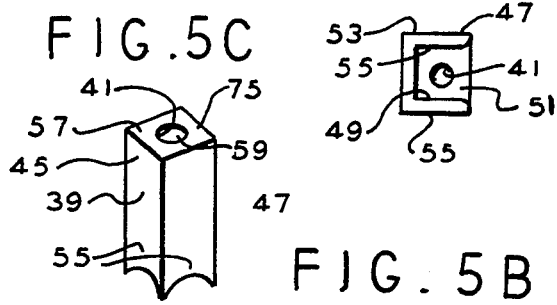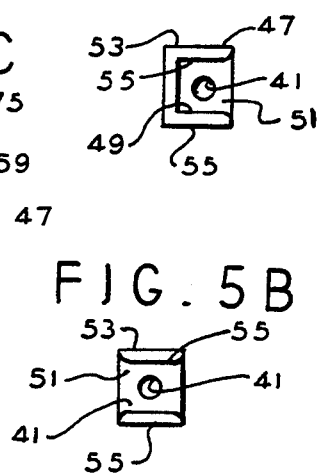

APPARATUS AND METHOD TO PROVIDE COMPRESSION FOR A LOCKED INTRAMEDULLARY NAIL

FIELD OF THE INVENTION

The present invention relates to a method and apparatus for achieving the fixation of long bone fractures and utilizing compression of an intramedullary nail.

DESCRIPTION OF PRIOR ART

Interfragmentary compression, achieved through the use of a plate and screws, is the usual method of producing absolute bony stability. Under the condition of absolute stability, bone units without callus formation. Compression plating is more useful in the treatment of non-unions and in osteomyelitis; absolute bony stability allows for primary bone healing to occur in the presence of infection. Immediate stability can also decrease porosity of host bone by early limb mobilization. Conversely, plate application may lead to continued porosity of the host by disruption of the vascular supply and plates and screw application may impart stress risers to the bony composite.

Intramedullary rodding applies osseous stability as a result of pressure generated between the recoil of a deformable rod and the rigid non-deformable bone. Generally, the intramedullary device shares the load with the bone acting as a gliding internal splint. In addition to mechanical stability, the intramedullary rod allows for a decrease in porosity of the host by early loading of the extremity.

FIGS. 7 and 8 discloses a means to achieve interfragmentary compression using an intermedullary rod (reference U.S. Pat. No. 5,100,404). As shown in the figure a concentric bolt system including inner and outer bolts 164 and 163, is employed. Outer bolt 163 includes a proximal flange 631 used to mount the alignment fixture in the manner discussed below. Inner bolt 164 is screwed into mating threads formed in the proximal end of the intramedullary nail 131. If controlled compression of the fracture fragments in relation to one another is desired, compression nut 162 and compression washer 161 are included on the outer bolt 163, then the nut 162 is turned by a wrench so as to urge proximal fragment 177 in the relative downward direction 171 and a distal fragment in an upward direction to a desired extent.

Outer bolt 163 is also used to hold the proximal alignment fixture 181 in place. This fixture, shown in FIG. 8, has a drilling guide hole 183 and mounting aperture 182. The fixture is positioned with the head of bolt 163 snugly disposed in the aperture 182 and the bottom surface 811 of the fixture 181 surrounding the aperture 182 rests on the flange 631 of the head of bolt 163 to hold the fixture in place. Set screw 184 locks the fixture to the head of bolt 163. The drilling guide 183 is used for guiding the drill 191 to drill the hole for a proximal locking screw. A difficulty with this system is that the guide is independent of the nail position which makes screw insertion difficult.

SUMMARY OF THE INVENTION

An object of the present invention is to provide an improved apparatus and method which achieves compression fixation of a bone.

Another object of the present invention is to provide an improved apparatus and method which achieves compression fixation of a bone while eliminating disruption of the vascular supply.

A still further object of the present invention is to provide an improved apparatus and method which decrease porosity of the host while obtaining compression fixation of a bone.

An additional object of the present invention is to provide an apparatus and method which achieves compression fixation of a bone while minimizing stress risers to the bony composite.

In accordance with the above objects, the present invention, in its broadest aspect as regards the apparatus, is directed to an apparatus for the fixation of a bone having a medullary canal for use with an intramedullary nail that has been inserted into the medullary canal, the intramedullary nail having a longitudinal axis and distal and proximal ends and apertures in the ends. This apparatus essentially comprises a first means, compression means, guide means and alignment means. The first means is in the form of an elongated first member having first and second ends, a central aperture, and a longitudinal axis aligned with said longitudinal axis of said intramedullary nail. The first end engages said bone adjacent said proximate end of said intramedullary nail. The compression means bears against said second end of said first member and applies compressive force to said bone through said first member. The guide means is disposed parallel to and spaced apart from said intramedullary nail; it has a proximal end and a proximal aperture. The alignment means is connected to said guide means and said first means and aligns said guide means with respect to said intramedullary nail to position the axis of the proximal aperture in said guide means along the axis of the proximal aperture in said intramedullary nail.

The present invention, in a narrower aspect as regards the apparatus, is directed to an apparatus for the fixation of a bone having a medullary canal for use with an intramedullary nail that has been inserted into the medullary canal, the intramedullary nail having a longitudinal axis and distal and proximal ends and apertures in the ends. This apparatus essentially comprises a first means in the form of a tubular member, compression means, guide means, alignment means and a rod member. The first means in the form of an elongated tubular member having first and second ends, a central aperture, and a longitudinal axis aligned with said longitudinal axis of said intramedullary nail. The first end direct engages said bone adjacent said proximate end of said intramedullary nail. The compression means bears against said second end of said tubular member and applies compressive force to said bone through said tubular member. The guide means is disposed parallel to and spaced apart from said intramedullary nail; it has proximal and distal ends and proximal and distal apertures. The alignment means is connected to said guide means and said tubular member and aligns said guide means with respect to said intramedullary nail to position the axes of the proximal and distal apertures in said guide means along the axes of the proximal and distal apertures, respectively, in said intramedullary nail.

The rod member is elongated and has a lower end having a first threaded end being adapted to be threadingly connected to said proximal end of said nail and a second threaded end which engages said compression means. The said first and second ends of said tubular member has upper and lower ends respectively, and a axially extending slot formed in said lower ends. This slot has a closed upper end and an open lower end, and said open lower end is defined by two spaced apart portions of the tubular member. The alignment means has first and second ends, the first end thereof is disposed within the slot in the tubular member and engages against the upper end of said slot. The portions of said tubular member which defines said central aperture are in sliding relationship with said second threaded end of said rod member.

The present invention, in its broadest aspect as regards the method, is directed to a method for locking an intramedullary nail, having proximal and distal ends and apertures in each end, to a bone, the method comprising locking the proximal aperture of the proximal end of the nail, after the distal aperture of the distal end of the nail is locked, by the following steps. Engaging a compression assembly on the proximal end of the nail and on the bone adjacent said proximal end of said nail. Then coupling a alignment fixture to the compression assembly. Then operating the compression assembly to compress the bone, adjacent said proximal end of said nail, to a predetermined stress level. Then using the alignment fixture to determine the location of the proximal aperture. Then drilling a proximal hole in the bone through the proximal aperture in the nail. Then inserting a locking screw through the drilled proximate hole and through the proximal aperture of the nail. Lastly, disabling and disengaging the compression assembly from the bone and nail.

Those, together with other objects and advantages which will become subsequently apparent reside in the details of construction and operation as more fully hereinafter described and claimed, reference being had to the accompanying drawings forming a part hereof, wherein like reference numerals refer to like parts throughout.

BRIEF DESCRIPTION OF THE DRAWINGS

FIG. 1 is a simplified elevation view of the apparatus and the femur experiencing fixation in accordance with the preferred embodiment of the present invention;

FIG. 2A is a simplified elevation view of the lower portion of the sleeve shown in FIG. 1;

FIG. 2B is a simplified side view of the lower portion of the sleeve shown in FIG. 1;

FIG. 3 is a simplified elevation view of the rod member and compression nut shown in FIG. 1;

FIG. 4A is a simplified elevation view of the intramedullary nail shown in FIG. 1;

FIG. 4B is a simplified top view of the intramedullary nail shown in FIG. 1;

FIG. 5A is a bottom view of a preferred embodiment of the sleeve shown in FIG. 1;

FIG. 5B is a bottom view of another embodiment of the sleeve shown in FIG. 1;

FIG. 5C is a perspective view of a preferred embodiment of the sleeve shown in FIG. 1;

FIG. 5D is a perspective view of another embodiment of the sleeve shown in FIG. 1;

FIG. 8 is a perspective view of a proximal alignment fixture of the prior art which includes the components shown in FIG. 7.

DETAILED DESCRIPTION OF THE INVENTION

Figure 7:
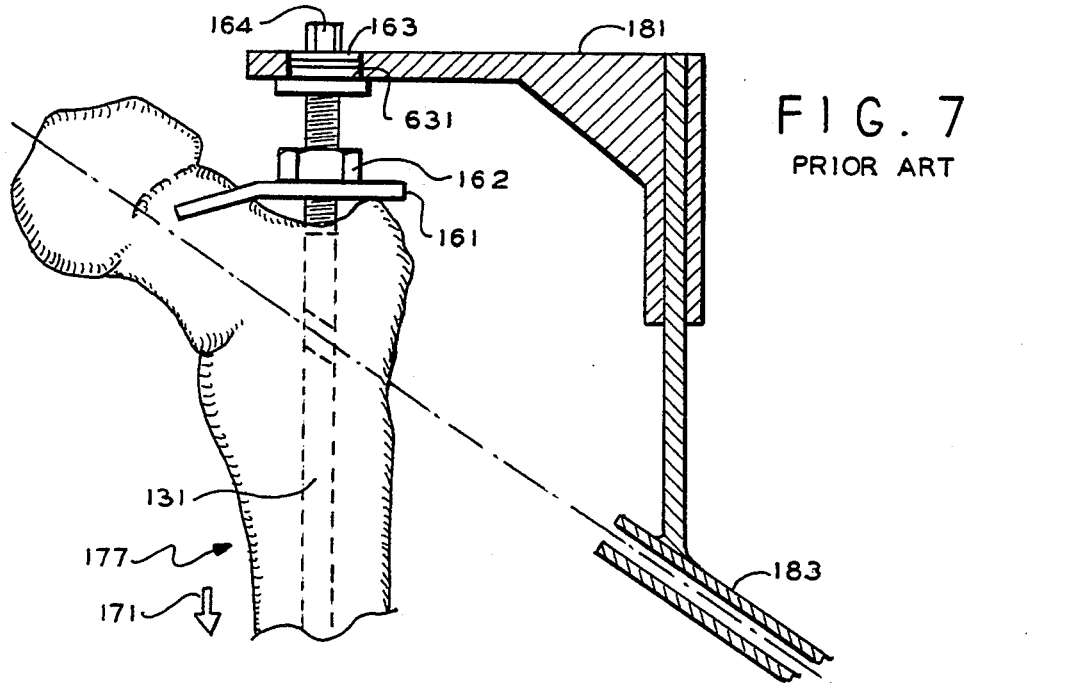
FIG. 7 illustrate in a partial vertical section the use of a prior art compression nut and washer and bolt system at the proximal end of an intramedullary nail.

Referring specifically to FIGS. 1 and 2, the apparatus for the fixation of a bone such as a femur, have a medullary canal, is generally designated by reference numeral 11. Disposed within the canal of the fractured femur 13 is a intramedullary nail 15, which has been inserted therein prior to its fixation. The nail 15 has a distal end 17, a proximal end 19, and a longitudinal axis 21. The distal end 17 has a pair of distal apertures 23 and a single proximal aperture in the form of a slot 25. An internally threaded aperture 26 is formed in the proximal end 19 of the nail 15. Referring specifically to FIG. 1, the apparatus 11 essentially comprises a compression assembly 16, an alignment fixture 18 and rod member 35.

The compression assembly 16 comprises a first means 27, in the form of an elongated tubular member which functions as a bone engaging means, and a compression means 29. The alignment fixture 18 comprises a guide means 31 and alignment means 33.

Referring now to both FIG. 1 and 2, the tubular member or sleeve 27 has first and second ends, 37 and 39, respectively, a central aperture or bore 41 extending the full length of the tubular member 27, and a longitudinal axis 43 which is aligned with the longitudinal axis 21 of the nail 15. The first end 37 of the sleeve 27 is also referred to as the first section. The first and second ends, 37 and 39, respectively, have upper and lower ends, 45 and 47, respectively, and the lower end 47 has an axially extending slot 49 (FIGS. 2A and 5A and 5C) formed therein. This slot 49 has a closed upper end 51 and an open lower end 53. The open lower end 53 of the slot 49 is defined by at least two spaced apart, opposing, lower portions or legs 55 of the lower end 47 of the tubular member 27. FIGS. 5A and 5C illustrates a three leg version and FIGS. 5B and 5D illustrates a two leg version. The ends of the lower portions 55 directly engage the femur bone 13 at point(s) adjacent the proximal end 19 of the nail 15. The central aperture 41 of the tubular member 27 is defined by central portions 57 which have smooth inner wall surfaces 59 to permit the tubular member 27 to freely slide up or down on the threaded rod member 35.

The elongated rod member 35 (FIG. 3) has lower and upper ends, 61 and 63, respectively. The lower end 61 of the rod member 35 is also referred to as the second section. The lower end 61 comprises first and second threaded ends, 65 and 67, respectively, and the first threaded end 65 is adapted to be threadably connected to an internally threaded proximal end 19 (FIGS. 4A and 4B) of the nail 15. The second end 67 of the lower end 61 has a threaded surface which extends at least slightly past the compression means 29 when the rod member 35 is attached to the nail 15 and the compression means 29 is in a position thereon for applying maximum compressive force to the bone 13 through the tubular means 27. The upper end 63 of the rod member 35 has an unthreaded surface and a first end 69 which is fixedly connected to a rotatable handle 71 which is used to rotate the rod member 35.

The compression means 29 constitutes a conventional, rotatable nut having a bore 72 with an internal thread which engages the threaded second end 67 of the rod member 35. The lower surface 73 of the nut 29 engages and bears against the upper surface 75 of the upper end 45 of the tubular member 27, which when tightened, applies a compressive force to the femur 13 through the tubular member 27.

Figure 6A:
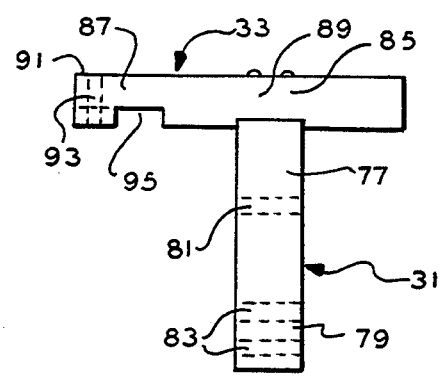
FIG. 6A is a simplified elevation view of the alignment fixture shown in FIG. 1.
Figure 6B:
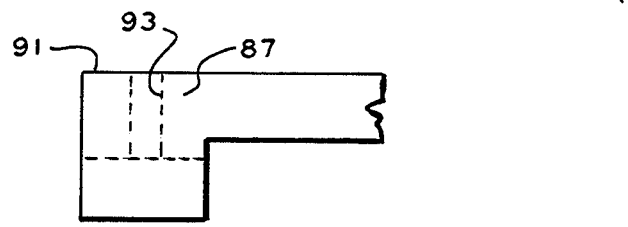
FIG. 6B is a simplified elevation view of a portion of the front end of the alignment means shown in FIG. 1.
Figure 6C:
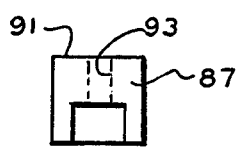
FIG. 6C is a simplified side view of the front end of the alignment means shown in FIG. 6B.
Figure 6D:
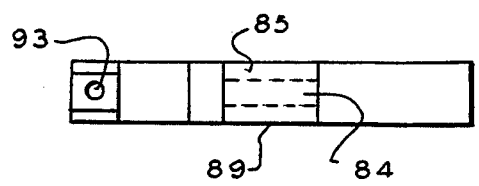
FIG. 6D is a simplified bottom view of the alignment means portion of the alignment fixture shown in FIG. 6A.

The guide means 31 (FIG. 6A) has proximal and distal ends, 77 and 79, respectively, and proximal and distal apertures, 81 and 83, respectively, therein. The proximal end 77 is connected through a slot 84 formed in the center portion 85 of the second end 89 of the alignment means 33 and the guide means 31 is disposed parallel to and spaced apart from the nail 15.

The alignment means 33 (FIGS. 6A–6D) has first and second ends, 87 and 89, respectively, which are connected to the tubular member 27 and the guide means 31. The first end 87 is disposed within the slot 49 of the tubular member 27 and the upper end 91 of the first end 87 engages against the upper end 51 of the slot 49 and moves up and down with the tubular member 27 it engages. The alignment means 33 functions to align the guide means 31 with respect to the nail 15, so that it positions the axes of the proximal and distal apertures, 81 and 83, respectively, in the guide means 31, along the axes of the proximal and distal apertures, 25 and 23, respectively, in the nail 15. A central bore 93 is formed in the first end 87 of the alignment means 33 to permit it to freely move with the tubular member 27. Another slot 95 is formed on the underside of the first end 87 to accommodate the trochanter portion 97 of the femur 13.

After the intramedullary nail 15 is conventionally inserted in the medullary canal of the femur 13, the apparatus 11 is disposed on the proximal portion of the femur 13 and the rod member 27 is inserted through the bores 72, 41, and 93 of the nut 29, tubular member 27, and alignment means 33, respectively, and into the threaded aperture 26 of the nail 15, where it is tightly joined to the proximal end 19 of the nail 15. Then the distal end 17 of the nail 15 is conventionally locked to the distal portion of the femur 13 through a pair of distal apertures 23 by a pair of locking screws 103. The distal portion of the femur 13 can be locked by utilizing the instant apparatus 11 by using the distal end 79 of the guide means 31 which is connected to the alignment means 33; this would involve drilling a pair of distal holes in the bone 13 through the distal apertures 23 in the nail 15. Proper alignment of the distal apertures 23 of the nail 15 with the drilled distal holes 23 in the bore 13 is achieved by drilling these distal holes 23 after first aligning them through the distal apertures 83 in the guide means 31 and then disposing the drill bit of the drill (not shown) through said distal apertures 83.

The method of locking the proximal aperture 25 of the proximal end 19 of the nail 15, after first locking the distal apertures 23 of the distal end 17 of the nail 15, comprises the following steps:

A. Engaging the compression assembly 16 and more specifically the lower end 47 of the tubular member 27 on the proximal end 19 of the nail 15 and on the femur 13 adjacent the proximal end 19 of the nail 15;

B. Coupling the alignment fixture 18 to the compression assembly 16; the aforementioned steps are accomplished by disposing the tubular member 27 on the proximal end 19 of the nail, and connecting the front end or first end 87 of the alignment means 33 within the slot 49 of the tubular member 27 so that both elements bores 93 and 41 are aligned, then inserting the rod member 35, with the nut 29 positioned in its uppermost position on the rod member 35, through the central bore 41 of the rod member 35 and the bore 93 of the alignment means 39 and tightly engaging its first threaded end 65 within the threaded aperture 26 of the nail 15. then the guide means 31 is inserted within the slot 84 of the alignment means 33.

C. Operating the compression assembly 16 to compress the bone 13 adjacent said proximal end 19 of the nail 15 to a predetermined stress level; this step is accomplished by tightening the nut 29 against the sleeve 27 by a torque wrench 99 until the desired stress level is achieved as indicated by the several strain gauges 101 disposed on the femur 13 adjacent the fracture - this results in the nail 15 moving upward relative to the sleeve 27.

D. Using the alignment fixture 18 for determining the -location for the proximal aperture or slot 81; this step is accomplished by viewing the femur 13 through the proximate slot 25 in the guide means 31.

E. Drilling a proximal hole in the bone 13 through the proximal aperture 25 in the nail 15; this step is achieved by the use of a drill or reamer.

F. Inserting a locking screw 105 through the drilled proximate hole and through the proximal aperture 25 of the nail 15; this is accomplished by installing the screw 105 into the reamed hole of the femur 13 and the aligned slot 25.

G. Disabling and disengaging the compression assembly 16 from the bone 13 and nail 15. This is accomplished by backing off the nut 29 which permits the sleeve 27 to disengage from the femur 13 and release the stress on the femur 13.

While the invention has been shown in a preferred and in an alternative embodiment thereof, numerous changes or modifications may occur to workers in the art without departure from the spirit and scope of the invention.

What is claimed is:

1. An apparatus for fixation of a bone having a medullary canal for use with an intramedullary nail that has been inserted into the medullary canal, the intramedullary nail having a longitudinal axis and distal and proximal ends and apertures in said ends, comprising:

a compression assembly for providing interfragmentary compression to said bone, comprising a first means and a compression means;

said first means in the form of an elongated first member having first and second ends, central portions defining a central aperture, and a longitudinal axis, adapted to be aligned with said longitudinal axis of said intramedullary nail, said first end for engaging only said bone adjacent said proximate end of said intramedullary nail;

said compression means, bearing against said second end of said first member, for applying compressive force to said bone through said first member;

guide means, disposed parallel to and spaced apart from said intramedullary nail, having a proximal end and a proximal aperture; and alignment means, connected to said guide means and said first means, for aligning said guide means with respect to said intramedullary nail to position the axis of the proximal aperture in said guide means along the axis of the proximal aperture in said intramedullary nail.

2. A fixation apparatus as recited in claim 1, wherein said first member comprises a tubular member.

3. A fixation apparatus as recited in claim 1, wherein said first and second ends of said first member has upper and lower ends respectively, and an axially extending elongated slot formed in said lower end thereof.

4. A fixation apparatus as recited in claim 3, wherein said slot has a closed upper end.

5. A fixation apparatus as recited in claim 4, wherein said alignment means has first and second ends, the first end thereof disposed within said slot and engaged against the upper end thereof.

6. A fixation apparatus as recited in claim 5, wherein said slot has an open lower end.

7. A fixation apparatus as recited in claim 1, further comprising an elongated rod member which has a lower end having a first threaded end, said threaded end being adapted to be threadingly connected to said proximal end of said intramedullary nail.

8. A fixation apparatus as recited in claim 7, wherein said lower end of said rod member has a second threaded end which engages said compression means.

9. A fixation apparatus as recited in claim 6, wherein said open lower end of said slot is defined by two spaced apart portions of the lower end of said first member.

10. A fixation apparatus as recited in claim 8, wherein said central portions of said first member which define said central aperture being in sliding relationship with said second threaded end of said rod member.

11. A fixation apparatus as recited in claim 1, wherein said guide means has a distal end and a distal aperture, and wherein said alignment means aligns said guide means to position the axis of said distal aperture in said guide means along the axis of the distal aperture in said intramedullary nail.

12. A fixation apparatus as recited in claim 1, wherein said first end of said first means engages said bone directly adjacent said proximal end of said intramedullary nail.

13. A fixation apparatus as recited in claim 1, wherein said aperture in said proximal end of said intramedullary nail forms an axially extending elongated slot therein.

14. An apparatus for fixation of a bone having a medullary canal for use with an intramedullary nail that has been inserted into the medullary canal, the intramedullary nail having a longitudinal axis and distal and proximal ends and apertures in said ends, comprising:

first means in the form of an elongated tubular member having first and second ends, a central aperture, and a longitudinal axis aligned with said longitudinal axis of said intramedullary nail, said first end for directly engaging said bone adjacent said proximate end of said intramedullary nail, compression means, bearing against said second end of said tubular member, for applying compressive force to said bone through said tubular member, guide means, disposed parallel to and spaced apart from said intramedullary nail, having proximal and distal ends and proximal and distal apertures, alignment means, connected to said guide means and said tubular member, for aligning said guide means with respect to said intramedullary nail to position the axes of the proximal and distal apertures in said guide means along the axes of the proximal and distal apertures, respectively, in said intramedullary nail, and an elongated rod member having a lower end having a first threaded end being adapted to be threadingly connected to said proximal end of said nail and a second threaded end which engages said compression means, wherein said first and second ends of said tubular member has upper and lower ends respectively, and an axially extending slot formed in said lower end, wherein said slot has a closed upper end and an open lower end, and said open lower end being defined by two spaced apart portions of the tubular member, wherein said alignment means has first and second ends, the first end thereof disposed within the slot in the tubular member and engaged against the upper end of said slot, and wherein said portions of said tubular member which defines said central aperture being in sliding relationship with said second threaded end of said rod member.

15. A method for locking an intramedullary nail having proximal and distal ends and apertures in each end, to a bone, the method comprising locking the proximal aperture of the proximal end of the nail, after the distal aperture of the distal end of the nail is locked, by the steps of:

engaging a compression assembly having first and second sections, the second section engaging only the proximal end of the nail and the first section engaging only on the bone adjacent said proximal end of said nail;

coupling an alignment fixture to the compression assembly;

operating the compression assembly to compress the bone adjacent said proximal end of said nail to a predetermined stress level;

using the alignment fixture for determining the location of the proximal aperture;

drilling a proximal hole in the bone through the proximal aperture in the nail;

inserting a locking screw through the drilled proximate hole and through the proximal aperture of the nail; and disabling and disengaging the compression assembly from the bone and nail.

16. A method according to claim 15 wherein the first section includes a tubular member having a lower end, disposed on the bone adjacent said proximal end of said nail, and wherein, those portions of the bone which are engaged by the lower end of the tubular member are compressed.

* * * * *